US005923818A

United States Patent [19]

Kautto

[11] Patent Number: 5,923,818

[45] Date of Patent: Jul. 13, 1999

[54] WATER FOG SPRAYING SYSTEM FOR INFRARED RADIANT DRYERS

[75] Inventor: Jorma Kautto, Vantaa, Finland

[73] Assignee: IRT Finland Oy, Espoo, Finland

[21] Appl. No.: 08/754,150

[22] Filed: Nov. 22, 1996

[30] Foreign Application Priority Data

Nov. 23, 1995 [FI] Finland ................................ 950491 U

[51] Int. Cl.[6] .......................... A61M 16/00; A01G 15/00; D06F 31/00

[52] U.S. Cl. ................................ 392/391; 239/2.1; 68/59

[58] Field of Search .................................... 392/379, 391, 392/383, 492, 397, 485, 478; 239/548, 550, 554, 566, 2.1; 427/428; 68/5 R

[56] References Cited

U.S. PATENT DOCUMENTS 4,998,359 3/1991 Rhynaer .................................. 239/566
5,117,482 5/1992 Hauber .................................... 392/379
5,180,330 1/1993 Bertrand .................................. 392/379
5,212,763 5/1993 Arold ...................................... 392/379
5,755,383 5/1998 Joseph .................................... 239/860

*Primary Examiner*—Teresa Walberg
*Assistant Examiner*—Daniel Robinson
*Attorney, Agent, or Firm*—Smith-Hill and Bedell

[57] ABSTRACT

A water fog spraying system for infrared radiant dryers includes a spraying tube (9) for spraying water fog onto a desired object, and infeed (6) and control means (7) for feeding water into the water line of the spraying tube (9). The spraying tube (9) includes a water line pipe (2) with nozzles (3) attached thereto and a jacket (1) adapted about the water line pipe (2), the jacket acting as the load-bearing structure of the spraying tube (9) and having openings made thereto at the nozzles (3).

6 Claims, 1 Drawing Sheet

WATER FOG SPRAYING SYSTEM FOR INFRARED RADIANT DRYERS

Figure 1:
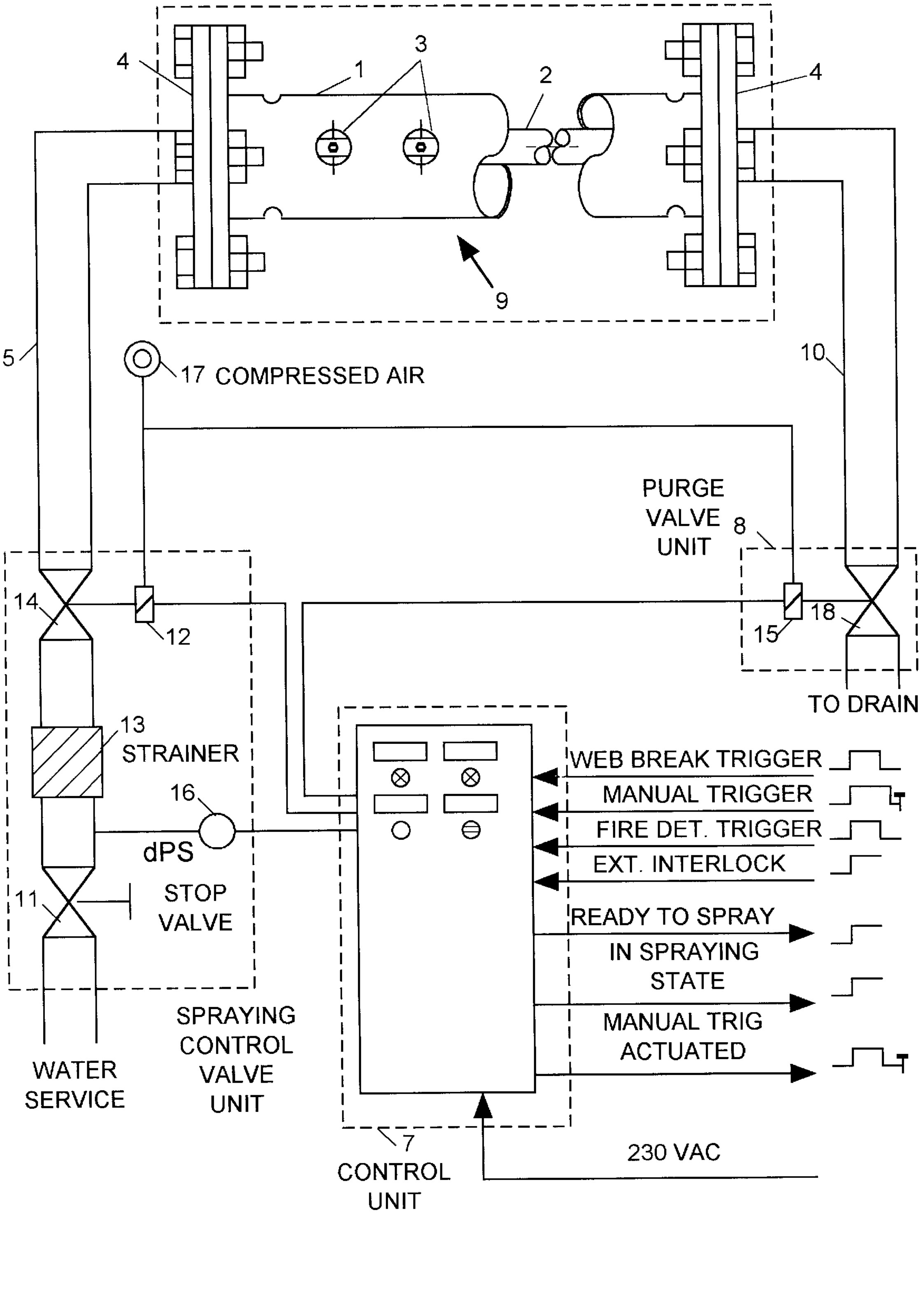

The invention relates to a water fog spraying system for use in infrared radiant dryers.

The system according to the invention is particularly suited for use in conjunction with infrared radiant dryers of the paper industry. However, the system may be broadly used in conjunction with any web-like material processing.

Since the surface temperatures in IR dryers are above the ignition point of a paper web and the continual trend in the industry toward maximized efficiency necessitates the use of higher surface temperatures, the risk of web fires in infrared radiant dryers has grown in the recent years.

Up till now, electric infrared radiant dryers have been protected by conventional building sprinklers operated either automatically or by manually actuated valves. A problem in the use of such equipment has been that they use hundreds, if not even thousands, of liter of water per fire, requiring a laborious cleaning of the paper machine before the next web tail threading. This shortcoming lengthens the duration of the web break and increases the workload of personnel. Also the risk of damage and short circuits in electrical equipment is involved with the use of large extinguishing water volumes.

It is an object of the present invention to provide such a water fog spraying system for infrared radiant dryers that is easy to install and is free from problems related to excessive use of extinguishing water or a high water-spray exit pressure imposed on the surrounding equipment.

The water fog spraying system according to the invention is based on a water fog spraying tube design comprised of an inner water line pipe equipped with water-atomizing nozzles and of a load-bearing supporting jacket, which coaxially encloses the water line pipe, the jacket having openings made thereto at the water-atomizing nozzles for directing the fog jets on the desired object.

More specifically, the fog spraying system according to the invention is characterized by what is stated in the characterizing part of the protective claim.

The invention offers significant benefits.

By virtue of the atomizing nozzles, smaller amounts of water can be used, whereby damage to the paper web or other associated equipment is reduced to a very minimum. Any water dripping from the nozzles remains inside the supporting jacket and may thus be drained by way of a small slope, whereby minimal leaks caused by, e.g., piping leaks will not cause blotting or holes in the web. Owing to its simple structure, the installation and commissioning of the system become straightforward operations, and the installed system requires little footprint at the installation site. By being enclosed in the interior of the jacket, the nozzles are protected against dirt and mechanical damage. Smooth outer surface of the jacket prevents adherence of debris to the spraying tube during a web break. Condensation and dripping of water is prevented by automated purging of water from the water line pipe and drainage of the jacket interior.

In the following the invention is described, the single FIGURE of greater detail by way of an exemplifying embodiment illustrated in the appended drawing in which is a schematic block diagram of a water fog spraying system according to the invention.

Referring to the diagram, the system installation comprises spanning a water fog spraying tube 9 with atomizing nozzles 3 transverse over the web. The operation of the system is based on flooding the potential combustion space in the dryer with fog of atomized water, which during its evaporation absorbs the combustion energy from its surroundings, purges oxygen away from the combustion area and moistens the combusting and/or combustible material and its environment, thus preventing fire from expanding and extinguishing a fire in the paper web material.

The amount of water consumption by the system is minimized. When connected to a normal water service of 6–7 bar pressure, the water-atomizing capacity of the spraying tube is typically in the order of 5.0–6.0 l/min per linear meter over the web.

The spreading volume of atomized water may be divided in two zones comprising

1) Central mist zone in which the droplet size is larger and which forms the body of the fog jet of atomized water. The central mist zone can be extended in a controlled manner to a defined area and thus needs to be directed toward the most probable nucleus of fire.
2) Fog zone with a very small droplet size. This portion of the atomized water jet easily escapes with air streams over a larger area thus performing smooth moisturizing of the environment and efficient cooling of the air.

The effective extinguishing area of the central and fog zones are dependent on the pressure in the spraying system line, the alignment of the spraying tube 9 and the position of the nozzles 3 in the spraying tube 9.

The spraying tubes 9 are fabricated to dimension for installation on site and are provided with conventional support means at their ends. The direction alignment of the atomizing nozzles is adjustable by the end flanges.

Typically, the spraying tubes 9 are made from jacketed acid-proof steel pipe. The jacket 1 is a load-bearing element and encloses in its interior a smaller-diameter water line pipe 2. The installation to the surrounding structures such as those of a paper machine is either stationary, or in special cases, movable during the water fog spraying operation.

Both ends of the spraying tube are provided with connectors for a water infeed service line 5 and a drain line 10. The valve unit 6 may be placed either on the operating or driving side of the paper machine. The drain line 10 with valves is placed to the opposite side of the machine with respect to the infeed line. It must be noted that the length of the drain line 10 also affects the fill speed of the water line pipe of the spraying tube 9 and purging of air therefrom.

The water line of the spraying tube 9 is automatically purged free from water after each spraying operation, whereby dripping of water is cut off rapidly and condensation on the spraying tube surface is avoided. The spraying tube 9 and the water piping 5, 10 are installed to a sufficient slope to facilitate removal of water therefrom after the spraying operation.

The valve unit 6 comprises the following parts:

A stop valve 11 permits separation of the system from the pressurized water service during a maintenance operation, for instance. A pressostat 16 installed on the line monitors pressure in the water line of the spraying tube. Impurities which could plug the nozzles are removed by means of a strainer 13. The spraying valve 14 is provided with a pneumatic actuator 17 and a solenoid valve 12. A control unit 7 is provided for the open/close operation of the solenoid valve. The valve unit 6 is factory-assembled on a mounting base. Valve connections are provided for a standard 1" pipe.

The purging valve unit 8 comprising a pneumatic actuator 17 and a solenoid valve 15 is designed into a modular unit factory-assembled on a mounting base. Valve connections are provided for standard 1" pipe.

The system requires the following signals, which are formed in the control unit 7:

—web break spraying trigger signal

—manual trigger signal

—fire detector trigger signal (optional)

—CR (counter-radiator) spraying enable or other interlock signal (optional)

—water line pressure OK signal from pressostat.

The control unit 7 sends the automation system the following status and alarm information:

—ready to spray

—in spraying state

—manual trigger actuated

The system controls the following functions:

—water line control valve open/close

—purge valve open/close.

The control unit 7 is fully enclosed and contains necessary feed-throughs. Each group of the spraying system is provided with a dedicated control unit. Alternatively, the control unit 7 may be replaced by a programmable logic control unit and control panel capable of implementing the required control functions.

The operation of the water fog spraying system according to the invention is outlined as follows:

Provided that the stop valve 11 is open and the water service pressure is detected to be at a proper level, the pressostat 16 gives a positive contact signal to the control unit 7. If none of the three possible trigger signals for starting the spraying operation are valid, the control unit keeps the "Standby for spraying" indicator light turned on. Then, the request for starting the water fog spraying can be received in three alternative manners in the form of:

1) a web break spraying signal from the automation system or the IRT programmable logic control unit, 2) a manual trigger signal from a machine-mounted operator pushbutton, or 3) a fire detector alarm signal from the automation system or the IRT programmable control unit.

Any of these requests can trigger the system into the spraying state. Power to the IR radiant heaters will be latest cut off by the system state feedback signal to the process control computer. Also a provision for disabling the restarting of the IR radiant heaters during the ongoing spraying operation must be arranged.

Depending on the source of the spraying request, the system operation is controlled as follows:

1) The web break spraying request related to the machine operation may be caused by a web break, slackening of the web, IR radiator power-down signal or a combination of these. The request for spraying controls the spraying valve 14 immediately open and allows water at line pressure to enter the water line pipe of the spraying tube 9. The control unit 7 keeps the spraying valve 14 open for a preset time. Trigger of such web break spraying request may be arranged to occur, e.g., during each web break, whereby the spraying system is used to counteract the start of a fire. The duration of the spraying cycle may be adjusted in the range 5–10 s, for instance. If the dryer is provided with counter-radiators, they must be hot to permit spraying of water on them.

2) The manual trigger signal releases the same functions as a web break spraying request, with the exception that the spraying cycle is continued until the trigger pushbutton is released, whereafter spraying of water fog is still continued for the duration of the preset spraying time. Thus, the shortest manually triggered spraying cycle is equal to that triggered by the automatic trigger signals.

3) The spraying cycle may be triggered by a fire detector alarm signal received from the automation system. Then, the spraying cycle is arranged to last longer that triggered in sequence (1). In practice, the such a fire extinguishing cycle is adjusted to last about 30–60 s. The fire detector alarm signal is an option in the system operation.

After the spraying cycle is completed, the system remains for short time of about 30–60 s waiting for, e.g., a repeated manual trigger signal. If no new trigger signal is received, the purge valve 18 opens and allows the water contained in the piping 9 and 10 to drain. Dripping from the spraying tube 9 is also stopped quickly hereafter.

The system is also provided with a disable input connected to external interlocks. This facility is necessary, e.g., when the infrared radiant dryer contains counter-radiators or other equipment requiring that the equipment is hot at the trigger instant of the spraying system. Thus, the external interlock can prevent the system from spraying water fog on a cold radiator. In this state, the system is in the "locked" state.

Obviously, the control unit 7 may be replaced by programmable logic controller.

Water flow rate per each spraying tube 9 is dependent on the cross-machine web width. For typical web widths, a 1" dia. piping is suitable.

The water fog spraying system according to the invention is not intended to replace an automatic sprinkler system or other general-purpose fire extinguishing equipment in the machine hall.

I claim:

1. A water fog spraying system for infra red radiant dryers, comprising:

a water line pipe with nozzles attached thereto, a jacket having first and second opposite ends, first and second support members attached to the jacket at opposite respective ends thereof, the water line pipe extending through the jacket and being supported relative to the jacket by the support members, and said jacket having openings therein aligned with said nozzles, and water infeed means for feeding water to the water line pipe.

2. A water fog spraying system according to claim 1, wherein the water line pipe has first and second opposite ends and the water infeed means is connected to the water line pipe at the first end thereof and the system further comprises a purge valve connected to the water line pipe at the second end thereof for draining water from the water line pipe and a control unit for controlling both the water infeed means and the purge valve.

3. A system according to claim 1, wherein the water infeed means comprises a manually operated stop valve and a spraying valve, and the system further comprises a control unit for controlling the spraying valve.

4. A water fog spraying system for infra red radiant dryers, comprising:

a water line pipe with atomizing nozzles attached thereto for generating a fog of atomized water, a jacket through which the water line pipe extends in radially spaced relationship, said jacket acting as a load-bearing structure for the water line pipe and having openings therein aligned with said nozzles for permitting fog generated by the nozzles to leave the jacket, and water infeed means for feeding water to the water line pipe.

5. A water fog spraying system for infra red radiant dryers, comprising:

a water line pipe with a plurality of atomizing nozzles attached thereto and spaced apart therealong for generating a fog of atomized water, a jacket through which the water line pipe extends in radially spaced and substantially coaxial relationship, said jacket acting as a load-bearing structure for the water line pipe and having openings therein aligned with said nozzles for permitting fog generated by the nozzles to leave the jacket, and water infeed means for feeding water to the water line pipe.

6. A water fog spraying system according to claim 1, wherein the water line pipe extends through the jacket in radially spaced and substantially coaxial relationship therewith.

* * * * *